United States Patent [19]

Jordan

[11] Patent Number: 4,721,572
[45] Date of Patent: Jan. 26, 1988

[54] PURFICATION OF BLOOD CLOTTING FACTORS AND OTHER BLOOD PROTEINS ON NON-CARBOHYDRATE SULFATED MATRICES

[75] Inventor: Robert E. Jordan, Walnut Creek, Calif.

[73] Assignee: Miles Laboratories, Inc., Elkhart, Ind.

[21] Appl. No.: 754,569

[22] Filed: Jul. 12, 1985

[51] Int. Cl.$^4$ .............................................. B01D 15/08
[52] U.S. Cl. .................................. 210/635; 210/198.2; 210/502.1; 210/656; 502/401; 502/402; 502/407
[58] Field of Search ..................... 502/401, 402, 407; 210/198.2, 502.1, 635, 656, 927

[56] References Cited

U.S. PATENT DOCUMENTS

| | | | |
|---|---|---|---|
| 3,920,625 | 11/1975 | Andersson et al. | 530/382 |
| 4,022,758 | 5/1977 | Andersson et al. | 530/382 |
| 4,086,222 | 4/1978 | Lindquist et al. | 210/635 X |
| 4,296,096 | 10/1981 | Pierce | 424/49 |
| 4,324,689 | 4/1982 | Shah | 502/401 |
| 4,350,760 | 9/1982 | Nicholas et al. | 210/635 X |
| 4,415,665 | 11/1983 | Mosbach et al. | 435/179 |
| 4,447,416 | 5/1984 | Menache-Aronson | 424/101 |
| 4,505,818 | 3/1985 | Mukoyama | 210/198.2 X |
| 4,606,825 | 8/1986 | Crane et al. | 210/656 X |
| 4,637,994 | 1/1987 | Tani et al. | 502/401 X |

OTHER PUBLICATIONS

D. Menache et al, *Blood*, 64 (6), 1220–1227 (Dec. 1984), "Coagulation Factor IX Concentrate: Method of Preparation and Assessment of Potential In Vivo Thrombogenicity in Animal Models".

J. P. Miletich et al, *Alalytical Biochemistry*, 105, 304–310 (1980), "The Synthesis of Sulfated Dextran Beads for Isolation of Human Plasma Coagulation Factors II, IX and X".

"TRISACRYL ® GF 2000", Product Information No. 203108, Reactifs IBF, Societe Chimique Pointet Girard, 92390 Villeneuve-La-Garenne (France).

J. Schutyser et al, "Affinity Chromatography and Related Techniques", TCJ Gribnau et al ed., Elsevier Scientific Publishing Co., 1982, pp. 143–153.

*Primary Examiner*—Richard V. Fisher
*Assistant Examiner*—W. Gary Jones
*Attorney, Agent, or Firm*—James A. Giblin; Pamela A. Simonton

[57] ABSTRACT

There is disclosed a non-carbohydrate sulfated matrix and the use thereof to isolate and purify blood clotting factors and other blood proteins by a procedure involving the adsorption of at least one of such factors and proteins onto the non-carbohydrate sulfated matrix followed by elution of such factors and proteins onto the non-carbohydrate sulfated matrix followed by elution of such factors and proteins from the matrix.

7 Claims, No Drawings

PURFICATION OF BLOOD CLOTTING FACTORS AND OTHER BLOOD PROTEINS ON NON-CARBOHYDRATE SULFATED MATRICES

FIELD

This invention relates to a non-carbohydrate synthetic gel matrix that is useful in a process to isolate and purify blood clotting factors and other blood proteins using affinity chromatographic techniques.

DESCRIPTION OF THE PRIOR ART

Many useful blood fractions and proteins may be obtained from blood and blood plasma by known techniques.

Andersson et al., U.S. Pat. Nos. 3,842,061 and 3,920,625, disclose a cross-linked sulfated polysaccharide gel matrix adsorbing agent and the use thereof to isolate and purify antithrombin and blood coagulation factors, respectively, from animal tissue materials such as blood, blood products or plasma fractions.

Menache-Aronson et al., U.S. Pat. No. 4,447,416, the production of an intermediate purified non-thrombogenic factor IX concentrate containing factor IX in major therapeutic amounts and containing factors II, VII and X in minor, non-thrombogenic amounts.

The sulfated matrices used to date all have been based on the use of carbohydrate as the backbone. Although such carbohydrate matrices has been useful especially in laboratory-scale separations, it has become evident that, for large-scale production work, gels having greater strengths and flow capacity and resistance to microbial attack would be desirable.

DESCRIPTION OF THE INVENTION

According to this invention, there is provided a sulfated, synthetic, non-carbohydrate gel matrix adsorbing agent comprising a sulfatable polymer selected from a synthetic organic gel matrix prepared by polymerization or copolymerizaation of at least one polymerizable organic monomer and from silica particles followed by sulfation of the polymer backbone by a sulfating agent. In another aspect of this invention, there is provided a process for isolating and purifying blood coagulating, or clotting, factors and other blood proteins comprising contacting blood, plasma, plasma protein concentrates, or tissue culture fluids containing blood coagulating factors or other blood proteins with the sulfated synthetic gel matrix adsorbing agent according to this invention.

The sulfated synthetic gel matrix adsorbing agent may be any organic polymeric material that is sulfatable and this is useful in affinity chromatographic separation operations. Examples of suitable synthetic gel matrices include polyhydroxylated acrylates and methoacrylates, silica particles, and polyvinylbenzene wherein the hydroxyl groups or benzene moiety can be sulfated by reaction of the hydroxyl groups or benzene moiety with a suitable sulfating agent such as, for example, sulfonyl chloride, chlorosulfonic acid and the like.

Preferably, the sulfated synthetic gel matrix according to this invention comprises a sulfated synthetic polyhydroxylated acrylate of methacrylate or a polyhydroxy silica particle.

An especially useful sulfated polyhydroxylated acrylate gel matrix is that derived from copolymerization of the monomer, N-acryloyl-2-amino-2-hydroxymethyl-1,3-propane diol, which is commercially available under the trademark TRISACRYL ® (Reactifs IBF, France).

An especially useful sulfated polyhydroxy silica particle material is that derived from sulfation of the polyhydroxy silica material commercially available under the trademark NuGel ® P-NP (Separation Industries, Metachem, N.J., U.S.A.).

Any conventional procedure for sulfating an organic hydroxyl group or aromatic (i.e. benzene) nucleus may be used to sulfate the synthetic gel matrix. A convenient sulfation procedure useful to sulfate the TRISACRYL and NuGel matrices mentioned above is a modification of the method reported by Miletech et al., *Analytical Biochemistry*, 105, 304–310 (1980), involving the use of chlorosulfonic acid in pyridine.

Among the blood clotting factors and other blood proteins which may be isolated and purified according to the process of this invention by using the sulfated, synthetic, non-carbohydrate gel matrix of the invention are factor IX, factor X, factor II, factor VII, VIII protein C, protein S, prothrombin, tissue plasminogen activator (TPA) and the like.

The blood coagulating, or clotting, factors and other proteins thus obtained, whether from plasma or tissue culture fluids using biotechnology, can be formulated into pharmaceutical preparations for therapeutic use. The pharmaceutical preparations may be treated by known means to render them free of infectious microorganisms such as bacteria and viruses and the like, including hepatitis B virus and the AIDS-causing agents (ARV, HTLV-III, and LAV agents). Such treatments include sterile filtration, heat treatment in the wet or dry state, chemical treatment, ultraviolet irradiation, and treatment with colloidal silica.

The following examples illustrate but a few embodiments of the present invention and are not to be construed as limiting in scope. All parts and percentages are by weight and all temperatures are in degrees Celsius unless otherwise indicated.

EXAMPLES

A. Preparation of sulfated matrices for adsorption of coagulation proteins

Example 1. Preparation of sulfated Trisacryl

Trisacryl is a synthetic, non carbohydrate gel matrix prepared by the copolymerization of the monomer N-acryloyl-2-amino-2-hydroxymethyl-1,3-propane diol. Trisacryl GF 2000 is manufactured by Reactifs IBF (France) and was obtained as an aqueous suspension.

1200 ml of suspended Trisacryl GF 2000 was dehydrated on a sintered glass funnel by sequential washes of distilled water (5 × 1200 ml), methanol (5 × 1200 ml) and acetone (5 × 1200 ml). The acetone-containing cake was spread on an aluminum foil surface and heated with an incandescent lamp in a fume hood until the powder was thoroughly dried (14 hours). The yield of dry Trisacryl powder from this treatment was 321 grams.

The sulfation reaction was carried out by a modification of the method previously described for dextran beads by Miletich et al (Analytical Biochemistry, 105, 304–310, 1980). The trisacryl powder was added with stirring to a solution of chlorosulfonic acid in pyridine obtained by the dropwise addition of 428 mls of acid to 2.14 liters of pyridine in a dry ice/ethanol bath. The solution was heated to 70 degrees C. to completely dissolve the pyridinium before addition of the trisacryl powder. Once added the suspension was stirred until the powder had adsorbed all of the liquid. The reaction mixture was maintained at 70 C. for 2 hours and then at 50 C. for 16 hours.

The wet trisacryl cake was transferred to scintered glass funnels on vaccum flasks attached to a water aspirator. Remaining pyridine solution was collected and combined with the first wash effluents for disposal. The gel was washed with a total of 50 liters of 2M NaCl adjusted to pH 10. The gel was then further washed with 50 liters of distilled water at pH 10. The final weight of the washed gel was 1580 grams.

The sulfated trisacryl gel was equilibrated before use in 10 volumes of a buffer consisting of 0.05M sodium citrate pH 6.5 and 0.10M sodium chloride. The equilibrated gel was then packed in the desired chromatographic column.

Example 2. Sulfation of polyhydroxy silica

Sulfation of polyhydroxy silica (NuGel P-NP obtained from Separation Industries, Metuchen, NJ) was carried out in a similar fashion to that described for Trisacryl in Example 1 above. A quantity of dry glass beads (10 grams) was added to a solution which had been prepared by the addition of 12.5 ml chlorosulfonic acid to 65 ml of pyridine as described in Example 1. The suspension was heated at 70 C. for 16 hours after which the pyridine solution was removed by filtration and the glass beads rapidly washed with 50 volumes of 2M NaCl solution at pH 10. The glass beads were then washed with 50 volumes of distilled water. Sulfation of the material could be readily confirmed by a modification of the colorimetric method described by Smith et al (P. K. Smith, A. K. Mallia and G. T. Hermanson, Anal. Biochem. 109, 466-473, 1980).

The ability of the sulfated polyhyroxysilica gel to adsorb coagulation factors IX and X was tested. To 10 ml aliquots of a solution of redissolved PTC powder (0.6% w/v) in 0.05M sodium citrate pH 6.5 containing 0.1M NaCl was added 2 grams of either the sulfated or the non-sulfated polyhydroxy silica gel. The suspension was mixed on a tube rocker for 15 minutes after which the suspension was centrifuged at low speed to pellet the gel. The presence of F.IX and F.X activities was assayed in the respective supernatants as well as in the starting PTC solution and are listed in Table 1.

TABLE 1

Factor X and IX activities in PTC solution adsorbed with sulfated and non-sulfated polyhydroxysilica

|  | F. IX U/ml | F. X U/ml |
| --- | --- | --- |
| Starting PTC solution | 2.6 | 13.4 |
| Supernatant of adsorption with non-sulfated polyhydroxy silica | 5.1 | 13.4 |
| Supernatant of adsorption with sulfated polyhydroxy silica | 1.3 | 5.9 |

As is evident from the data in the Table, the supernatant of the adsorption with the sulfated gel contains considerably less of both F.IX and F.X activity than the starting PTC solution. Some activation of F.IX is apparent after contact with the non-sulfated material. Nevertheless, the data confirm that the sulfated polyhydoxysilica gel possesses the abilty to adsorb coagulation factors in apparent contrast to the non-sulfated form.

B. Use of Sulfated Trisacryl in preparation of partially purified coagulation factors

Example 1. Use of Sulfated Trisacryl for the Preparation of a Partially Purified Factor IX from PTC by Gradient elution (3001-34)

PTC powder, a dried, vitamin K dependent coagulation factor-containing material which is an intermediate step in the commercial process for the production of Factor IX concentrate, was redissolved at 1% w/v in 0.05M sodium citrate containing 0.1M NaCl, pH 6.5. After dissolution of the powder, the solution was adsorbed with powdered, fumed silica (Aerosil 380, a product of DeGussa) at a 1% w/v ratio for 45 minutes at 42 C. The suspension was centrifuged and the insoluble pellet of Aerosil and adsorbed materials was discarded. The supernatant was filtered and cooled to 10 C. The chilled solution was applied to a column (17 cm × 14 cm) containing sulfated Trisacryl and equilibrated in 0.05M sodium citrate containing 0.1M NaCl at pH 6.5. Column flow rates were approximately 10 L/hr. Material not binding to the column and eluting as a breakthrough peak was discarded. The applied sample was followed by a volume of equilibration buffer sufficient to reduce the protein in the eluate to an A280 <0.1. A 40 liter gradient of NaCl from 0.1M to 0.6M was then applied to the column and 1 liter fractions collected and analyzed for their protein content and immunologically detectable amounts of coagulation Factors IX and X as well as Protein C.

The elution profile of the column is shown in FIG. 1. Fractions containing immunologically identifiable amounts of Factors IX, X and Protein C are indicated in the Figure. Protein C and Factor X were poorly resolved and eluted early in the gradient at a sodium chloride concentration of approximately 0.15-0.3M. Factor IX was observed to elute later in the gradient at approximately 0.4M NaCl although there was some overlap with F. X.

The Factor IX-containing regions of the elution of similar column runs were pooled and dialyzed vs. 0.015M sodium citrate containing 0.12M NaCl. After concentration and sterile filtration, a partially purified F.IX preparation was obtained for animal studies with the following characteristics:

| Factor IX activity | 30.2 units/ml |
| --- | --- |
| protein concentration | 4.41 mg/ml |
| F. IX spec. activity | 6.85 units/mg |
| NAPTT | |
| 1:10 | 163 sec |
| 1:100 | 312 sec |

Example 2. Rapid chromatography of DEAE eluate on sulfated Trisacryl with quantitation of Factors II, VII, IX and X A concentratae containing vitamin K-dependent clotting factors was obtained by contacting Effluent I plasma with DEAE Sephadex and eluting the adsorbed gel as follows. After removal of the spent Effluent I, the DEAE gel was sequentially washed with (1) 0.2M sodium bicarbonate, (2) 0.3M sodium bicarbonate and (3) 0.2M sodium chloride containing 0.01M sodium citrate, pH 6.5. The Factor IX and other vitamin K-dependent factors were then eluted from the DEAE gel with a buffer containing 0.55M NaCl and 0.01M sodium citrate, pH 6.5. The eluate was diafiltered against six volume exchanges of 0.05M sodium citrate containing 0.1M NaCl, pH 6.5. 73 L of eluate were obtained and aliquots were frozen for subsequent chromatographic studies. The content of clotting factors in the dialyzed eluate expressed as total units is given in Table 2.

TABLE 2 content of Vitamin K-dependent clotting factors in the dialyzed eluate from DEAE Sephadex contact of eluate I

|  | units/ml | total units |
| --- | --- | --- |
| Factor II (prothrombin) | 12.0 | 876,000 |
| Factor VII | 2.5 | 182,130 |
| Factor IX | 6.6 | 481,800 |
| Factor X | 12.6 | 919,800 |
| Protein C | positive for antigen | |
| Protein S | positive for antigen | |

For the purpose of determining maximum flow characteristics of the sulfated trisacryl gel, a column of the following dimensions was constructed: height=5 cm, diameter=25 cm. 8.7 liters of the DEAE eluate described above was treated with Aerosil 380 at 0.25% w/v at 5 C. for 60 minutes. The insoluble Aerosil was removed by filtration and the clarified eluate applied to the sulfated trisacryl column at 24 liters/hour. (Flow rates of up to 60 liters per hour were obtained with this column configuration without visible deformation of gel or marked loss of column performance). The elution profile of the column is shown in FIG. 2. After application of the clarified DEAE eluate, the column was washed with 0.1M NaCl, 0.05M sodium citrate, pH 6.5. Separate step elutions were then carried out at 0.275M NaCl and 0.55M NaCl respectively for differential elution of clotting factors. Both of the latter elution steps included 0.05M sodium citrate, pH 6.5. Table 3 describes the presence of various clotting factors in each purification step.

TABLE 3

Quantitation of clotting factors in purification scheme outlined in Example 2

| Step | Total Units | | Presence of Antigen | |
| --- | --- | --- | --- | --- |
|  | F. IX | F. X | F. II | P. C. |
| DEAE eluate | 57420 | 145,290 | + | + |
| Post Aerosil DEAE eluate | 57936 | 119,950 | + | + |
| Unbound column peak | 5076 | 43,990 | + | + |
| 0.275 M NaCl peak | 25376 | 60,512 | − | + |
| 0.55 M NaCl peak | 14076 | 1,173 | − | − |

While the separations obtained in this example are not optimum, this chromatography is illustrative of the fact that resolution of vitamin K-dependent factors is possible at very high flow rates. Of particular note is the observation that Factor II (prothrombin) elutes in the unbound eluate and is not detectable in later elution steps. This was confirmed in similar chromatographic runs using specific F.II clotting assays. Protein C antigen is observed to co-chromatograph with F. X. The recovery of F. X and F.IX activities in the various elution steps is in good agreement with the total amounts of respective activities applied to the column.

Example 3. Stepwise elution of clotting factors from sulfated trisacryl with emphasis on the removal of F.X. from the F.IX To a column of sulfated trisacryl with the dimensions described in Example 1 was applied 5 liters of a solution of DEAE eluate prepared as described in Example 2. No Aerosil adsorption of this solution was carried out. Rather the sodium chloride concentration of the applied DEAE eluate was adjusted to 0.3M prior to application. The column was also pre-equilibrated in 0.3M NaCl, 0.05M sodium citrate, pH 6.5. After application of the sample, the column was washed with equilibration buffer to reduce the A280 of the column eluate to <0.2. The Factor IX was then eluted in a single step with a buffer containing 0.55M NaCl. The recoveries of Factors IX and X are given in Table 4.

TABLE 4

Recoveries of Factors IX and X in the sulfated trisacryl chromatography of Example 3.

| Step | A280 | F. IX | | F. X | |
| --- | --- | --- | --- | --- | --- |
|  |  | units/ml | tot u | units/ml | tot u |
| DEAE eluate (5 liters)* | 5.41 | 4.9 | 24,580 | 14.5 | 72,500 |
| Unbound peak (17.8 L) | 1.22 | 0.59 | 10,500 | 4.1 | 72,980 |
| 0.55 M NaCl-eluted peak (8.64 L) | 0.60 | 1.75 | 15,120 | undetectable | |

This example demonstrates that it is possible to effectively remove F.X from the final F.IX preparation as eluted from the sulfated trisacryl. Since Factor X is, in our experience, the most troublesome and most likely contaminant from among the other vitamin K-dependent factors, it follows that the levels of other clotting factors such as F.II are also likely to be very low in the F.IX peak described here. Indeed, in other similar chromatographies, prothrombin was found to be undetectable in F.IX peaks.

What is claimed is:

1. In a method of isolating and purifying at least one of the group of blood coagulation factors and proteins selected from the group consisting of factors IX, X, II, VII, VIII, protein C, protein S, prothrombin, and tissue plasminogen activator, from a source of said blood coagulation factors and proteins selected from blood, blood plasma, plasma concentrates, and tissue culture fluids, obtained by means of biotechnology techniques, by the steps of
    (a) contacting the blood, blood plasma, plasma concentrates, and tissue culture fluids with at least one affinity chromatography adsorbing agent,
    (b) separating the non-adsorbed solution from the non-adsorbing agent, and
    (c) eluting the adsorbed blood coagulation factors and proteins from the adsorbing agent using an eluant effective to elute the desired factor(s) and protein(s),
the improvement comprising using as the adsorbing agent a sulfated, synthetic, non-carbohydrate affinity chromatography gel matrix adsorbing agent comprising a sulfatable polymer, said sulfatable polymer selected from the group consisting of
    (i) a synthetic organic affinity chromatography gel matrix prepared by polymerization of at least one polymerizable organic monomer, and
    (ii) polymeric silica particles,
said sulfatable polymer having been treated by a process consisting essentially of treating with a sulfating agent so as to provide a multiplicity of sulfate groups bound directly to the polymer backbone.

2. A method according to claim 1 wherein said sulfatable polymer is said synthetic organic affinity chromatography gel matrix prepared by polymerization of at least one polymerizable organic monomer and is selected from the group consisting of sulfated polyhydroxylated acrylates and methacrylates, and sulfated polyvinylbenzene.

3. A method according to claim 2 wherein the polymer backbone of said sulfated polyhydroxylated acrylate is obtained by copolymerization of the monomer, N-acryloyl-2-amino-2-hydroxymethyl-1,3-propane diol.

4. A method according to claim 1 including the step of treatment to render said blood coagulation factors and proteins non-infective by infectious viruses, including hepatitis virus, bacteria, and retroviruses, including the AIDS-causing agent(s).

5. A sulfated, synthetic, noncarbohydrate affinity chromatography gel matrix adsorbing agent comprising a sulfatable polymer, said sulfatable polymer selected from the group consisting of a synthetic organic affinity chromatography gel matrix prepared by polymerization of at least one polymerizable organic monomer, and polymeric silica particles, said sulfatable polymer having been treated by a process consisting essentially of treating with a sulfating agent so as to provide a multiplicity of sulfate groups bound directly to the polymer backbone.

6. An affinity chromatography gel matrix adsorbing agent according to claim 1 wherein said sulfatable polymer is said synthetic organic affinity chromatography gel matrix prepared by polymerization of at least one polymerizable organic monomer and is selected from the group consisting of sulfated polyhydroxylated acrylates and methacrylates, and sulfated polyvinylbenzene.

7. An affinity chromatography gel matrix adsorbing agent according to claim 6 wherein said sulfated polyhydroxylated acrylate is obtained by copolymerization of the monomer, N-acryloyl-2-amino-2-hydroxymethyl-1,3-propane diol.

* * * * *